United States Patent
Maul et al.

(12) 
(10) Patent No.: US 6,274,727 B1
(45) Date of Patent: Aug. 14, 2001

(54) METHOD FOR PRODUCING SHAPED AND UNSHAPED POLYOL MASSES

(75) Inventors: Karin Maul, Darmstadt; Eugen Schwarz, Bensheim, both of (DE)

(73) Assignee: Merck Patent Gesellschaft mit beschrankter Haftung (DE)

( * ) Notice: Subject to any disclaimer, the term of this patent is extended or adjusted under 35 U.S.C. 154(b) by 0 days.

(21) Appl. No.: 09/308,135

(22) PCT Filed: Nov. 3, 1997

(86) PCT No.: PCT/EP97/06046

§ 371 Date: May 14, 1999

§ 102(e) Date: May 14, 1999

(87) PCT Pub. No.: WO98/22094

PCT Pub. Date: May 28, 1998

(30) Foreign Application Priority Data

Nov. 15, 1996 (DE) ............................................. 196 47 282
Oct. 6, 1997 (DE) ............................................. 197 43 986

(51) Int. Cl.[7] ............................... C07H 1/06; C07H 1/08; B01D 9/00

(52) U.S. Cl. ............................. 536/127; 127/15; 127/16; 127/30; 127/58; 127/60; 426/658; 426/660; 568/863; 568/872

(58) Field of Search ............................... 536/127; 127/15, 127/16, 30, 58, 60; 126/658, 660; 568/863, 872

(56) References Cited

U.S. PATENT DOCUMENTS

| | | | |
|---|---|---|---|
| 4,497,846 | * | 2/1985 | Boursier et al. ..................... 426/660 |
| 4,693,750 | | 9/1987 | Bauer et al. . |
| 5,139,795 | * | 8/1992 | DuRoss ................................... 426/3 |

FOREIGN PATENT DOCUMENTS

| | | |
|---|---|---|
| 3506276 | 4/1986 | (DE) . |
| 4439858 | 5/1996 | (DE) . |
| 19509805 | 9/1996 | (DE) . |
| 19615418 | 10/1997 | (DE) . |
| 1 526 020 | * 9/1978 | (GB) . |

* cited by examiner

*Primary Examiner*—Nathan M. Nutter
(74) *Attorney, Agent, or Firm*—Millen, White, Zelano, & Branigan, P.C.

(57) ABSTRACT

The invention relates to a composition, comprising one or more polyols, which has prolonged deformability and can be processed to give tablets, compacts or boiled sweets having improved properties.

16 Claims, No Drawings

METHOD FOR PRODUCING SHAPED AND UNSHAPED POLYOL MASSES

This application was filed under 35 U.S.C. 371 as the national phase of PCT application PCT/EP97/06046 filed Nov. 3, 1997.

The invention relates to a composition, comprising one or more polyols, which has a prolonged deformability and can be processed to give tablets, compacts or boiled sweets having improved properties.

Numerous publications and patent applications disclose compositions for the production of tablets, compacts or even boiled sweets (EP-A-0 240 773, EP-A-0 462 066 or DE-A1-43 16 537), in which all sorts of physiologically tolerable substances are used as excipients for pharmaceutical active compounds or flavourings. These include, in particular, cellulose derivatives and their salts, carbohydrates, sugars, water-soluble polymers such as N-vinylpyrrolidone/vinyl acetate copolymers, polyvinylpyrrolidone, polyvinyl alcohol, polyacrylic acid and its salts, polymethacrylic acid and its salts, polyalkylene oxides such as polyethylene oxide, polypropylene oxide and also copolymers of ethylene and propylene oxides, polysaccharides such as alginic acid, their alkali metal and ammonium salts, carrageenans, galactomannans, tragacanth, agar-agar, gum arabic, xanthan gum, chitin derivatives, such as chitosan, pectins, such as sodium carboxymethylamylopectin and starches and also mixtures of these water-soluble polymers. Water-soluble is in this case understood as meaning that, at 20° C., at least 0.5 g, preferably 2 g, of the polymer can optionally dissolve in colloidal form or dissolve with gel formation in 100 g of water.

In the production of tablets, coated tablets, lozenges or boiled sweets, good water solubility of the excipient matrix is of particular importance for bioavailability and rapid absorption.

Water solubility is admittedly also of importance for a pleasant taste and sensation in the mouth, but the surface composition and the taste sensation during sucking also play a relatively large part in this connection. In the case of the known excipient materials, this is nor afforded without problems. While one has a negative taste pattern, the others lead on account of their physical condition to irregular, granular surfaces or, on account of their short processability, to uneven, possibly sharp-edged surfaces.

Usually, premixtures are prepared in order to obtain a homogeneous distribution of an added active compound in the excipient matrix, the various components are fused with one another or the active compounds are mixed by kneading in an existing polymer melt. Problems in these processes are the uniform dose, the homogenous mixing and the continuous procedure.

For the administration of pharmaceutical active compounds in tablet, coated tablet or lozenge form, in order to guarantee a constant dose the active compound must be homogeneously dispersed in the excipient matrix. This is a particular problem when using poorly soluble active compounds.

The object of the invention is therefore on the one hand to make available a composition which can be carefully processed in a temperature range to give the desired products, i.e. to give tablets, compacts or boiled sweets, in which added active compounds are not damaged. The object of the invention is also to make available a process which can be carried out continuously, whereby tablets, compacts, lozenges or boiled sweets can be prepared which have a smooth surface which is also retained during sucking, and have a pleasant taste and sensation in the mouth and also a homogeneous dispersion of active compounds and flavourings contained therein. It is furthermore an object of the invention to make available compositions which can be employed in this process and, due to long deformability, can be processed in a simple manner to give the desired products.

The object is achieved by compositions comprising previously co-sprayed polyol, in particular by compositions comprising one or more polyols from the group consisting of xylitol, sorbitol or lactitol, maltitol, erythritol or mannitol, and optionally carbohydrates from the group consisting of starch, cellulose, and also, depending on the product, optionally one or more active compounds, one or more colourants, one or more natural sweeteners, one or more synthetic sweeteners, acidifying agents, flavourings, aromatizers and customary auxiliaries.

The object is also achieved by a process for the production of a plastic, shaped or unshaped material in which a composition consisting mainly of one or more polyols is extruded in a temperature range from 30 to 170° C. and optionally shaped. In particular, the object is achieved by previously co-sprayed compositions, which are extruded and the extrudate obtained in this manner is then processed further in subsequent shaping units.

It is known, for the production of lozenges, compacts or sweets, to extrude mixtures of the individual components and to fuse them with one another at temperatures below 200° C. The extrudate can be divided by calendering or by comminution using rotating knives into equal-volume, still-shapable pieces having a solid surface, which can be processed directly subsequently by compressing to give tablets. It is also known to add active compounds and other additives by means of suitable equipment during extrusion. It still causes problems here, however, even today to achieve a really homogeneous active compound mixture and to obtain a product having a really smooth surface.

Experiments have shown that compositions based on sorbitol, xylitol, lactitol or other substances analogous to sugar, such as maltitol, erythritol, mannitol or others which can optionally additionally contain carbohydrates from the group consisting of starch and cellulose, can be shaped in a simple manner to give extrudates which can be processed further readily and for a long time. Compositions which contain these polyols in the mixture can also be processed in the same manner and readily.

It was also found that polyol-containing materials which have a high xylitol content can be processed particularly readily. Those materials in particular have exceedingly good processing properties whose components have been pretreated before extrusion in the co-spraying process described in Patent Application DE 19617487.2 and processed together to give a finely divided powder. This powder employed for the extrusion is not only a mixture of two or more different powders but a powder in which even the individual particles consist of a mixture of the individual components as a result of the co-spraying, i.e. mixed crystals are obtained. In comparison with powder mixtures customarily used, these powders have a lower melting point, and plastic materials obtained therefrom are also deformable for a long time and readily after extrusion. This deformability can be further prolonged by the addition of suitable crystallization retardants known to the person skilled in the art, which can be added during the co-spraying. Advantageously, in compositions based on co-sprayed polyols or polyol mixtures according to the invention, the addition of plasticizers or flow-regulating agents which are otherwise necessary can be dispensed with.

Owing to the prior co-spray drying of the individual components, powders are obtained which, as they are formed and collected in the co-spraying process, can be continuously extruded. Between or during the processing stages of the co-spraying and the extrusion, active compounds, additives and customary pharmaceutical auxiliaries, such as fillers, lubricants, mould release agents, flow-regulating agents, plasticizers, colourants, stabilizers, acidifying agents, flavourings and aromatizers can be added to the powder mixtures.

Fillers which can be added are those generally known to the person skilled in the art, such as oxides of magnesium, aluminium, silicon and titanium, but also others.

If required, in certain cases suitable flow-regulating agents such as, for example, mono-, di- and triglycerides of the long-chain fatty acids, waxes, carnauba wax or lecithins can be added. In general, however, these additives are not needed in the compositions according to the invention.

Besides low molecular weight polyalkylene oxides such as polyethylene glycol, polypropylene glycol and polyethylene propylene glycol, polyhydric alcohols such as propylene glycol, glycerol and pentaerythritol and also sodium diethylsulphosuccinate, mono-, di- and triacetate of glycerol and polyethylene glycol stearate are also suitable as plasticizers, which can be added if necessary.

As lubricants, stearates of aluminium or calcium and also talc or silicones can be used.

As colourants, natural colouring agents can likewise be employed, as well as all colourants and pigments permitted as foodstuff additives.

Possible stabilizers are antioxidants, radical scavengers, stabilizers against microbial attack and photostabilizers.

Depending on the composition, all additives can be added in the concentrations familiar to the person skilled in the art, to be precise in concentrations such that the respective desired effect of the additive is achieved.

It is possible to add all additives during the extrusion. However, it is advantageous for uniform dispersion in the product to add soluble additives during the co-spraying process of the composition.

Insoluble additives can be mixed with the powder obtained by co-spraying and, if appropriate, the other components can be mixed mechanically before extrusion.

Owing to the prior co-spraying, mixtures are obtained which can be extruded with a high throughput to give deformable materials. These powder mixtures in this case require a lower energy input on account of the lower melting point and the improved plasticity, obviously produced by a modified structure of the powder employed.

Depending on the polyol or polyol mixture employed, during extrusion a certain energy input is thus necessary. This is thus dependent, as indicated, on the manner in which the polyol mixtures have been obtained, namely by simple mixing or co-spraying. The energy input can be effected mechanically by the extrusion process and the forces acting here. However, it can also be effected thermally by additional heating. There are specific differences here, the lowest amount of energy being necessary in the case of the co-sprayed polyol compositions. The polyol mixtures according to the invention can be extruded in the temperature range from 30 to 170° C., in particular from 40 to 110° C. For mixtures obtained by co-spraying, conditions have proved particularly suitable under which the energy input leads to a product temperature of approximately 70 to 110° C.

Whilst co-sprayed polyol mixtures can be extruded in a simple manner, the extrusion of mechanically mixed polyol combinations to give homogeneous products is not possible, as the various polyols have different melting points. In particular, non-co-sprayed mixtures which contain mannitol require a high energy input, as otherwise a coarse-grained extrusion product is obtained in which the mannitol crystals are present as such. For mannitol-containing mixtures, therefore, prior co-spraying is recommended. By means of subsequent extrusion, the energy input leading to a product temperature of up to 110° C. at the exit site, products having a smooth surface and good sucking behaviour are obtained after shaping. Mannitol-containing mixtures processed by the process according to the invention have particularly good product properties if at least two further polyols are contained therein in an amount of up to 10% by weight.

By means of comparison experiments, it was generally found that previously co-sprayed polyol compositions can be processed to give extrusion products having a smoother surface than if simply mixed compositions are employed for extrusion. If, for example, a commercially available spray-dried sorbitol (Karion Instant®) as a main component is extruded directly after simple mixing with the other components of the composition, after the extrusion, in which the product emerging has a temperature of about 100° C., and the subsequent shaping a product having a rougher surface is obtained than if a corresponding previously co-sprayed composition is used. If, however, another, likewise commercially available crystalline sorbitol (Neosorb®) is treated in the same manner, extrudates having smooth surfaces are obtained, which additionally have good sucking behaviour. In this case, however, a very high energy input is necessary, and thick rod diameters cannot be selected arbitrarily.

Depending on the composition of the mixtures and their past history, the choice of a certain extrusion process is therefore indicated. Extrusion can be carried out using double-screw extruders or plasticizing screws in which the energy input can take place by means of the screw and, if appropriate, additionally by heating. It is additionally possible, however, to carry out extrusion with heating using a compacting or transport screw. As variable parameters during extrusion, it is possible, inter alia, to alter the product input amount, the transport rate of the screw, the size of the outlet nozzle and the temperature.

On account of their good processing properties, the materials obtained by prior co-spraying by means of the process according to the invention can be pressed with good results through larger hollow diameters than are customarily used for corresponding products. A higher product throughput is thereby achieved.

Co-sprayed polyols from the group consisting of xylitol, sorbitol, lactitol, maltitol, erythritol and mannitol, their mixtures or mixtures with other polyols can be processed with particularly good results by the process according to the invention, one or more of these polyols in the mixture being processed by extrusion to give a plastic, shaped or unshaped material. Compositions have proved particularly suitable in which the polyols sorbitol and xylitol are contained in a quantitative ratio of 50:50 to 99:1, in particular of 65:35 to 98:2. Compositions in which the three polyols sorbitol, xylitol and mannitol are contained in the mixture have particularly good properties if these are contained in quantitative ratios of 90:1:9 to 70:29:1, in particular of 82:9:9. All sorts of additives can be added to polyol mixtures of this composition before extrusion. Such additives can be, for example, one or more active compounds, one or more colourants permitted as foodstuff additives, but also one or more natural and/or one or more synthetic sweeteners. These additives can be added on their own or together. Processing aids and additives customary in the pharmaceutical or foodstuffs industry can furthermore be added. These additives can be added constantly in a uniform dose using modern metering balances, as described in EP-B1-0 337 256, so that a composition which is always uniform is extruded.

The plastic shaped or unshaped materials obtained from the polyol compositions according to the invention after extrusion can be processed further by means of subsequent shaping units customarily used in the foodstuffs or pharmaceutical industry, such as, for example, engraved rollers or automatic rolling machines.

In comparison with products prepared in a known manner, products prepared from the materials according to the invention, such as tablets, compacts, lozenges or boiled sweets, have a significantly smoother surface, which is also retained during consumption and in particular on sucking. Dissolution in the mouth takes place much more uniformly, the originally very smooth surface also being retained. The formation of sharp edges is greatly reduced by these improved properties. These advantageous properties are particularly pronounced in products whose individual components have been mixed with one another by co-spraying before extrusion. Co-sprayed polyol compositions are also particularly highly suitable, on account of their lower melting point, for the extrusion process according to the invention, as incorporated active compounds, flavourings etc. are exposed to a lower temperature stress and the extrusion rod is still deformable for longer than usual; namely the product obtained additionally remains plastic, soft and deformable for approximately 1 to two minutes after extrusion. Furthermore, in comparison to extrudates customarily obtained, the choice of the rod diameter is most variable on account of the marked and good plastic behaviour of the extrudates according to the invention. These compositions after extrusion and shaping also show better sucking behaviour than known hitherto.

Compared with the conventional process, the process according to the invention has a number of advantages. These include, inter alia, the possibility of continuously being able to prepare powdered compositions with constantly equal concentrations of the individual components, which are extruded directly under more gentle conditions to give plastic shaped or unshaped materials and can be shaped in a subsequent process to give tablets, compacts, lozenges or boiled sweets. A particular advantage of the compositions according to the invention is that the products produced have far smoother surfaces, which are also retained during sucking. Furthermore, an advantageous flavour improvement is achieved by the prior co-spraying with the polyols according to the invention and, if appropriate, with mannitol. In particular, a chalky taste, as occurs in known antacids, is concealed by the compositions according to the invention. The bioavailability and absorption of incorporated active compounds is also increased hereby, as the tablets prepared are readily soluble on account of the excipient substances used and can be sucked without problem on account of their pleasant taste. This is of importance if a rapid activity is desired, as can be the case, for example, with contained analgesics.

If desired, the tablet prepared according to the invention can also be provided with a customary coating to improve the appearance or for the purpose of additional retardation of active compound release. It can be favourable for tablets with retarded active compound release if the tablet is prepared in close-cell porous form by one of the known techniques in order that it floats in the stomach and thereby resides longer.

Pharmaceutical active compounds in the sense of the invention are understood as meaning all substances having a pharmaceutical action and the lowest possible side effects if they are not decomposed under the processing conditions. The amount of active compound per dose unit and the concentration can vary within wide limits depending on the activity and release rate. Thus the active compound concentration can be in the range from 0.1 to 95, preferably from 5 to 80. Active compound combinations can also be employed. The compositions according to the invention are preferably suitable for the incorporation of those active compounds whose immediate biological availability is desired and which, together with the other constituents, produce an advantageous taste profile. Such active compounds can be antacids, analgesics, sedatives, relaxants or other pharmaceutical active compounds. Active compounds in the sense of the invention are also dietary physiological substances, such as vitamins, minerals and trace elements.

The examples given in the following are intended to illustrate the present invention, but they are not suitable for restriction of the invention thereto.

EXAMPLES

Table 1:
  Compositions:
  a mechanically mixed polyol composition
  b spray-dried sorbitol
  c P300 sorbitol
  d crystalline sorbitol

| Experiment No. | 1 | 2 | 3 | 4 | 5 | 6 | 7 | 8 |
|---|---|---|---|---|---|---|---|---|
| Composition | a | b | c | b | b | b | d | d |
| Throughput [kg/h] | 17 | 15 | 14 | 14 | 14 | 17 | 17 | 17 |
| tm E [° C.] | — | 90 | 100 | 92.5 | 92.5 | — | 101 | 103 |
| p 1 [bar] | 7 | 16 | 2 | 3 | 3 | 2 | 0 | 9 |
| t 1 S/l [° C.] | K | K | K | K | K | K | K | K |
| t 2 S/l [° C.] | 90 | 70 | 110/120 | 80 | 77 | 88 | 130 | 115 |
| t 3 S/l [° C.] | 90 | 50 | 110/120 | 80 | 77 | 90 | 130 | 115 |
| Perforated plate | 1 × 4.6 | 2 × 2 | 1 × 4.5 | 1 × 4.5 | 1 × 4.5 | 12 × 9 ov Teflon | 12 × 9 ov Teflon | 1 × 4.5 |
| Remarks | Start with water 20 bar, | Smooth surface | Product soft, | rel. smooth | Temperature optimization | Very smooth | crumbly, open- | rough surface, |

-continued

| Experiment No. | 1 | 2 | 3 | 4 | 5 | 6 | 7 | 8 |
|---|---|---|---|---|---|---|---|---|
| | more pressure with small nozzle | | extrudate breaks | extrudate, slight pulsation | experiment | extrudate, good surface condition | pore, no extrudate | roughness dependent on temperature |

What is claimed is:

1. A composition for the production of tablets, compacts or boiled sweets, comprising a mixture obtained by co-spraying at least two polyols, and optionally carbohydrates from the group consisting of starch and cellulose, extruding the compostion and optionally shaping the extruded composition.

2. Composition according to claim 1, comprising one or more polyols from the group consisting of xylitol, sorbitol, lactitol, maltitol, erythritol and mannitol.

3. Composition according to claim 1, comprising sorbitol and xylitol in a quantitative ratio of 50:50 to 99:1.

4. Composition according to claim 1, comprising sorbitol, xylitol and mannitol in a quantitative ratio of 90:1:9 to 70:29:1.

5. Tablets, compacts, lozenges, or boiled sweets, comprising a composition according to claim 1.

6. Tablets, compacts, lozenges, or boiled sweets according to claim 5, comprising an active compound.

7. Process for the production of a plastic shaped or unshaped material, wherein a composition according to claim 1 is extruded in a temperature range of from 30 to 170 degrees C, and optionally shaped.

8. Process according to claim 7, wherein the compostion is obtained by co-spraying and is extruded at a temperature below 110 degrees C.

9. Process for the continuous production of compacts for the foodstuffs industry and of solid administration forms for the pharmaceutical industry, wherein the plastics material prepared according to claim 7, which can be present in the form of a rod, is processed further in subsequent shaping.

10. Process according to claim 9, wherein further shaping is carried out on engraved rollers or in automatic rolling machines.

11. Process according to claim 7, wherein one or more active compounds, colorants, natural or synthetic sweeteners, acidifying agents, flavorings, aromatizers, or crystallization retardants are added continuously or by means of premixtures.

12. Compositions prepared by a process according to claim 7.

13. Tablets, compacts, lozenges or boiled sweets according to claim 12.

14. Composition according to claim 3, comprising sorbitol and xylitol in a quantitative ratio of 65:35 to 98:2.

15. Composition according to claim 4, comprising sorbitol, xylitol and mannitol in a quatitative ratio of 82:9:9.

16. Process for the production of a plastic shaped or unshaped material, wherein a composition according to claim 7 is extruded in a temperature range of from 40 to 110 degrees C., and optionally shaped.

* * * * *